United States Patent [19]
Hillman et al.

[11] Patent Number: 6,136,314
[45] Date of Patent: Oct. 24, 2000

[54] HISTONE FUSION PROTEIN

[75] Inventors: Jennifer L. Hillman, Mountain View; Surya K. Goli, Sunnyvale, both of Calif.

[73] Assignee: Incyte Pharmaceuticals, Inc., Palo Alto, Calif.

[21] Appl. No.: 09/353,688

[22] Filed: Jul. 14, 1999

Related U.S. Application Data

[62] Division of application No. 08/824,878, Mar. 26, 1997, Pat. No. 5,981,221.

[51] Int. Cl.[7] .............................. C12P 21/06; C12N 1/20; C12N 15/00; C07H 21/04; C07K 1/00

[52] U.S. Cl. ................... 424/192.1; 435/69.1; 435/252.3; 435/320.1; 536/23.1; 536/23.4; 536/23.5; 530/350

[58] Field of Search ...................... 424/192.1; 435/69.1, 435/252.3, 320.1; 536/23.1, 23.4, 23.5; 530/350

[56] References Cited

PUBLICATIONS

Goldknopf, I.L., et al., "Isopeptide linkage between nonhistone and histone 2A polypeptides of chromosomal conjugate–protein A24", *Proc Natl Acad Sci USA*, 74(3) : 864–868 (1977).

Palmer, D.K., et al., "Purification of the centromere–specific protein CENP–A and demonstration that it is a distinctive histone", *Proc Natl Acad Sci USA*, 88 (9) : 3734–3738 (1991).

Pehrson, J.R. et al., "MacroH2A, a Core Histone Containing a Large Nonhistone Region", *Science*, 257: 1398–1400 (1992).

Pehrson, J.R., et al., (GI 205275) GenBank Sequence Database (Accession M99065) National Center for Biotechnology Informatiion: National Library of Medicine, Bethesada, Maryland 20849 (205276).

Dobner, T., et al., "A novel divergently transcribed human histone H2A/H2B gene pair", *DNA Seq*, 1 (6) : 409–413 (1991).

Constanzi, C. And Pehrson, J.R. (GI 1711126), GenBank Sequence Database (Accession U79139), National Center for Biotechnology Information, National LIbrary of Medicine, Bethesda, Maryland 20894.

*Primary Examiner*—Ponnathapu Achutamurthy
*Assistant Examiner*—Tekchand Saidha
*Attorney, Agent, or Firm*—Incyte Pharmaceuticals, Inc.

[57] ABSTRACT

The present invention provides a human histone fusion protein (HFP) and polynucleotides which identify and encode HFP. The invention also provides expression vectors, host cells, agonists, antibodies and antagonists. In addition, the invention also provides methods for producing HFP and for treating or preventing disorders associated with expression of HFP.

4 Claims, 8 Drawing Sheets

```
5' NNC CAG GAG GGC TCA GGC CGA GAC ACC TTG CAG CCG CCG CCA CCG AGC
         9          18              27              36              45          54

CGC CGC TGT GCT CAC TGA TCC GCC AGG GCC ACC GCC ATG TCG AGC CGC GGT
    63              72              81              90              99         108
                                                     M   S   S   R   G

GGG AAG AAG TCC ACC AAG ACG TCC AGG TCT GCC AAA GCA GGA GTC ATC TTT
   117             126             135             144             153         162
    G   K   K   S   T   K   T   S   R   S   A   K   A   G   V   I   F

CCC GTG GGG CGG ATG CTG CGG TAC ATC AAG AAA GGC CAC CCC AAG TAC AGG ATT
   171             180             189             198             207         216
    P   V   G   R   M   L   R   Y   I   K   K   G   H   P   K   Y   R   I

GGA GTG GGG GCA CCC GTG TAC ATG GCC GCC GTC CTG GAA TAC CTG ACA GCG GAG
   225             234             243             252             261         270
    G   V   G   A   P   V   Y   M   A   A   V   L   E   Y   L   T   A   E

ATT CTG GAG CTG GCT GGC AAT GCA GCG AGA GAC AAC AAG AAG GGA CGG GTC ACA
   279             288             297             306             315         324
    I   L   E   L   A   G   N   A   A   R   D   N   K   K   G   R   V   T

CCC CGG CAC ATC CTG CTG GCT GTG GCC AAT GAT GAA GAG CTG AAT CAG CTG CTA
   333             342             351             360             369         378
    P   R   H   I   L   L   A   V   A   N   D   E   E   L   N   Q   L   L
```

```
        387           396           405           414           423           432
    AAA GGA GTC   ACC ATA GCC   AGT GGG GGT   GTG TTA CCC   AAC ATC CAC   CCC GAG TTG
     K   G   V     T   I   A     S   G   G     V   L   P     N   I   H     P   E   L 441           450           459           468           477           486
    CTA GCG AAG   AAG CGG GGA   TCC AAA TTG   GAA GCC ATC   ACA CCA CCC
     L   A   K     K   R   G     S   K   L     E   A   I     T   P   P 495           504           513           522           531           540
    CCA GCC AAA   AAG GCC GAC   AGC AAC AAC   TCC CAG AAG   CCT GTA TCT   AAA AAA GCA
     P   A   K     K   A   D     S   N   N     S   Q   K     P   V   S     K   K   A 549           558           567           576           585           594
    GGA GGC AAA   AAG GGG GCC   GAC AAC AAC   AAG AAG AAG   CAG GGT GAA   GTC AGT AAG
     G   G   K     K   G   A     D   N   N     K   K   K     Q   G   E     V   S   K 603           612           621           630           639           648
    GCA GCC AGC   GCC GAC AGC   AAC AAC CGA   GGG GAA CAC   CTG CCC GAC   GGT TTC ACA
     A   A   S     A   D   S     N   N   R     G   E   H     L   P   D     G   F   T 657           666           675           684           693           702
    GTC CTC TCC   ACC AAG AGC   CTC TTC CTT   GGC CAG AAG   CTG AAC CTT   ATT CAC AGT
     V   L   S     T   K   S     L   F   L     G   Q   K     L   N   L     I   H   S 711           720           729           738           747           756
    GAA ATC AGT   AAT TTA GCC   GGC TTT GAG   GTG GAG GCC   ATA ATC AAT   CCT ACC AAT
     E   I   S     N   L   A     G   F   E     V   E   A     I   I   N     P   T   N
```

FIGURE 1B

```
      765         774         783         792         801         810
GCT GAC ATT GAC CTT AAA GAT GAC CTA GGA AAC ACG CTG GAG AAA GGT GGC
 A   D   I   D   L   K   D   D   L   G   N   T   L   E   K   G   G 819         828         837         846         855         864
AAG GAG TTT GTG GAA GCT GTC CTG GAA CTC CGG AAA AAG AAC GGG CCC TTG GAA
 K   E   F   V   E   A   V   L   E   L   R   K   K   N   G   P   L   E 873         882         891         900         909         918
GTA GCT GGA GCT GTC AGC GCA GGC CAT GGC CTG CCT GCC AAG TTT GTG ATC
 V   A   G   A   V   S   A   G   H   G   L   P   A   K   F   V   I 927         936         945         954         963         972
CAC TGT AAT AGT CCA GTT TGG GGT GCA GAC AAG TGT GAA GAA CTT CTG GAA AAG
 H   C   N   S   P   V   W   G   A   D   K   C   E   E   L   L   E   K 981         990         999        1008        1017        1026
ACA GTG AAA AAC TGC TTG GCC CTG GCT GAT GAT AAG AAG CTG AAA TCC ATT GCA
 T   V   K   N   C   L   A   L   A   D   D   K   K   L   K   S   I   A 1035        1044        1053        1062        1071        1080
TTT CCA TCC ATC GGC AGC AGG GGC AAC GGT TTT CCA AAG CAG ACA GCA GCT CAG
 F   P   S   I   G   S   R   G   N   G   F   P   K   Q   T   A   A   Q 1089        1098        1107        1116        1125        1134
CTG ATT CTG AAG GCC ATC TCC AGT TAC TTC GTG TCT ACA ATG TCC TCT TCC ATC
 L   I   L   K   A   I   S   S   Y   F   V   S   T   M   S   S   S   I
```

FIGURE 1C

```
            1143           1152           1161           1170           1179           1188
      AAA ACG GTG TAC TTC GTG CTT TTT GAC AGC GAG AGT ATA GGC ATC TAT GTG CAG
       K   T   V   Y   F   V   L   F   D   S   E   S   I   G   I   Y   V   Q 1197           1206           1215           1224           1233           1242
      GAA ATG GCC AAG CTG GAC GCC AAC TAG GCT GAG CAA TGA CAG AAC CAG CTG CAC
       E   M   A   K   L   D   A   N 1251           1260           1269           1278           1287           1296
      CAT GTA CCC CAC CTT CAG TTT AAA AGA AAA AAA TCC CCT TCA CTC CTA CTG 1305           1314           1323           1332           1341           1350
      GGA GGT GGG ACC CCT TTC ATT TTC AGT TTT GCT CAT CTA GGG AAA ATA AGG CTT 1359           1368           1377           1386           1395           1404
      TGG TTT CCA GTT TAA TTG TTT TTG ACC TTC TAA AAT GTT TTT ATG TTA GCA CTG 1413           1422           1431           1440           1449           1458
      ATA GTT GGC ATT ACT GTT GTT AAG CAC TGT GTT CCA GAC CGT GTC TGA CTT AGT 1467           1476           1485           1494           1503           1512
      GTA ACC TAG GAG ATT TTA TAG TTT TAT TTT AAT GAA ACC CTG ATT GAC GCA CAG
```

FIGURE 1D

```
      1521          1530          1539          1548          1557          1566
CAG TGG GGA GAA CAG CGT CTT TTA CCT GTC ACC GAA GCC CAG GAA GCC CCG TTT 1575          1584          1593          1602          1611          1620
GTA AGC GTG TGT TGT GGT GCT TTA TTG TAC ATC CTC CAG TGG CGT TCT TTT TAC 1629          1638          1647          1656          1665          1674
TCT AAT GTT CTT TTG GTT TCC CCC CTC AGA AGA ATC ATG AAT TTG CAA CAG ACC 1683          1692          1701          1710          1719          1728
TAA TTT TTG GTT ACT TTT TGT CTT ATT GAT GGA TTT GAA AAT GAA AGA TTT AAT 1737          1746          1755          1764          1773          1782
AAG GCA AAG CAG AAT CTG TTG TCC TTA ATT ATA TTT GCA ATT TGG AAT TTG TGT 1791          1800          1809          1818          1827
GAG TTG ATT TAG TAA AAT GTT AAA CCG TTA AAA AAA GAA AAA AAA AA 3'
```

FIGURE 1E

```
  1  MSSRG---GKKKSTKTSRSAKAGVIFPVGRMLRYIKKGHP   2297753
  1  MSSRG---GKKKSTKTSRSAKAGVIFPVGRMLRYIKKGHP   GI 205276
  1  MSGRGKQGGKARAKAKTRSSRAGLQFPVGRVHRLLRKGNY   GI 31980

38  KYRIGVGAPVYMAAVLEYLTAEILELAGNAARDNKKGRVT   2297753
 38  KYRIGVGAPVYMAAVLEYLTAEILELAGNAARDNKKGRVT   GI 205276
 41  AERVGAGAPVYLAAVLEYLTAEILELAGNAARDNKKTRII   GI 31980

78  PRHILLAVANDEELNQLLKGVTIASGGVLPNIHPELLAKK   2297753
 78  PRHILLAVANDEELNQLLKGVTIASGGVLPNIHPELLAKK   GI 205276
 81  PRHLQLAIRNDEELNKLLGKVTIAQGGVLPNIQAVLLPKK   GI 31980

118  RGSKGKLEAIITPPPAKKAKSPSQKKPVSKKAGGKKGARK   2297753
118  RGSKGKLEAIITPPPAKKAKSPSQKKPVAKKTGGKKGARK   GI 205276
121  TESH--------------------------------HK   GI 31980

158  SKKQGEVSKAASADSNNRGEHLPDGFTVLSTKSLFLGQK   2297753
158  SKK-QGEVSKAASADSTTEGAP-TDGFTVLSTKSLFLGQK  GI 205276
127  AKGK----------------------------------  GI 31980

198  LNLIHSEISNLAGFEVEAIINPTNADIDLKDDLGNTLEKK  2297753
196  LQVVQADI--ASIDSDAVVHPTNTDFYIGGEVGSTLEKK   GI 205276
130  ---                                       GI 31980
```

HISTONE FUSION PROTEIN

This application is a divisional application of U.S. application Ser. No. 08/824,878, filed Mar. 26, 1997 now U.S. Pat. No. 5,981,221.

FIELD OF THE INVENTION

This invention relates to nucleic acid and amino acid sequences of a novel histone fusion protein and to the use of these sequences in the diagnosis, prevention, and treatment of disorders associated with cell proliferation and inflammation.

BACKGROUND OF THE INVENTION

Chromosomes store genetic information for living organisms and are essential for eukaryotic cell differentiation and function. Generally, chromosomes consist of one linear DNA molecule complexed with numerous proteins which are responsible for organizing the DNA into conformations suitable for gene replication and transcription. These conformations change at various stages of cell differentiation and are maintained and regulated by histones and nonhistone proteins.

Histones are small, basic proteins with molecular masses ranging from 11 kDa to 22 kDa. They are evolutionarily conserved in sequence and structure across species which emphasizes their critical role in gene structure. Five types of histones, termed H1, H2A, H2B, H3, and H4, exist in a variety of forms due to post-translational modifications of certain side chains. A common feature of histones is their high content of positively charged side chains, about one in four residues is either lysine or arginine. When a histone-DNA complex forms, the positive charges of the histone side chains neutralize the negative charges of chromosomal DNA. Specifically, H2A, H2B, H3, and H4, as well as nonhistone proteins, interact with repeats of 200 base pairs of chromosomal DNA to form nucleosomes. Then, H2A interacts with H1 to group the nucleosomes into second order structure. Higher-order structures of chromosomes involve the interaction of histones and chromosomal DNA with a series of nonhistone proteins.

Nonhistone proteins are important in assembling nucleosomes and providing a structural scaffold for chromosomal DNA. Nucleoplasmin and N1 protein are nonhistone proteins which bind H2A/H2B and H3/H4, respectively, for assembly of nucleosomes. Topoisomerase II is a nonhistone protein responsible for cleaving and resealing double-stranded DNA in the process of scaffolding chromatin fiber into chromosomes.

Histone and nonhistone structures also form linkages, the functional aspect of which is largely unknown. Post-translational ubiquitination of histones H2A and H2B and CENP-A, an unusual form of histone H3 localized to centromeric heterochromatin, provides examples of the histone-nonhistone linkages (Goldknopf, I. L. and Bush, H. (1977) Proc. Natl. Acad. Sci. U.S.A. 74:864–868; Palmer, D. K. et al. (1991) Proc. Natl. Acad. Sci. U.S.A. 88:3734–3738). mH2A, identified in rat liver nucleosomes, is another histone-nonhistone fusion protein which contains a core histone and a large nonhistone region (Pehrson, J. R. and Fried, V. A. (1992) Science 257:1398–1400). The amino terminus of mH2A resembles full-length H2A, and the nonhistone region contains a leucine zipper-like motif and a basic domain rich in Lys and Arg (Pehrson and Fried, supra).

The discovery of a novel H2A-like protein and the polynucleotides encoding it satisfies a need in the art by providing new compositions which are useful in the diagnosis, prevention and treatment of disorders associated with cell proliferation and inflammation.

SUMMARY OF THE INVENTION

The present invention features a novel histone fusion protein hereinafter designated HHFP and characterized as having similarity to a rat histone-nonhistone fusion protein mH2A and a human histone H2A.

Accordingly, the invention features a substantially purified HHFP having the amino acid sequence shown in SEQ ID NO:1.

One aspect of the invention features isolated and substantially purified polynucleotides that encode HHFP. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode HHFP. The present invention also features antibodies which bind specifically to HHFP, and pharmaceutical compositions comprising substantially purified HHFP. The invention also features methods for stimulating cell proliferation using HHFP or its agonist, and for treating or preventing disorders associated with cell proliferation and inflammation using an antagonist of HHFP.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of HHFP. The alignment was produced using MacDNASIS PRO™ software (Hitachi Software Engineering Co., Ltd., San Bruno, Calif.).

FIGS. 2A and 2B show the amino acid sequence alignments among HHFP (SEQ ID NO:1), rat mH2A (GI 205276; SEQ ID NO:3) and human H2A (GI 31980; SEQ ID NO:4). The alignment was produced using the multisequence alignment program of DNASTAR™ software (DNASTAR Inc, Madison Wis.).

DESCRIPTION OF THE INVENTION

Figure 3A:
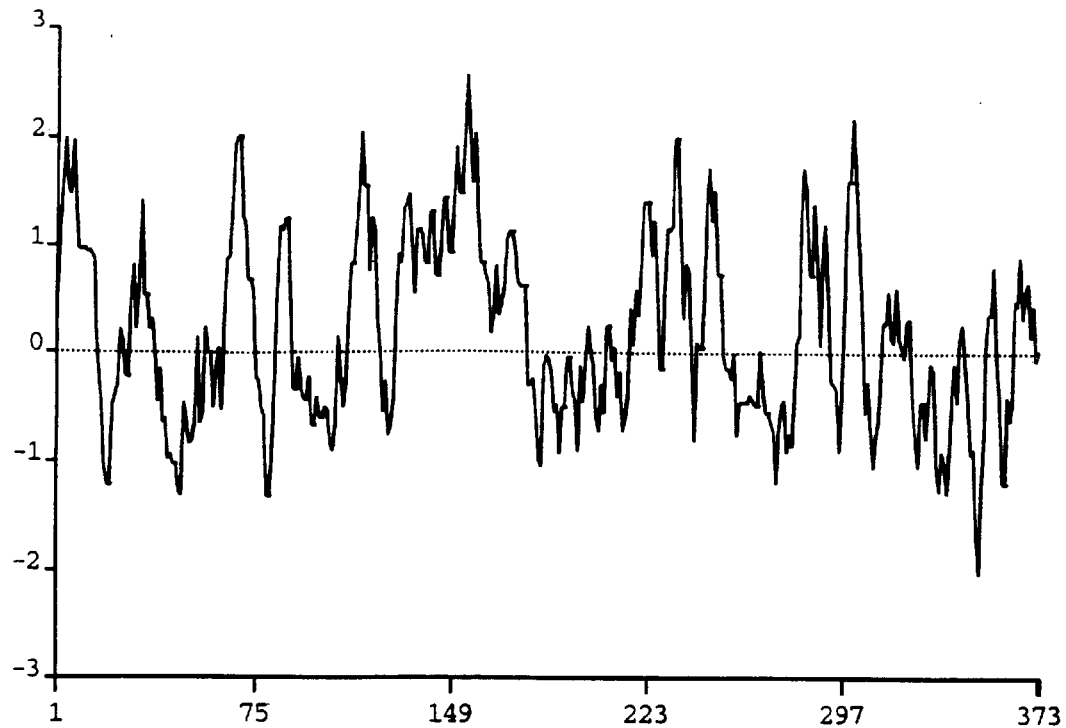
FIGS. 3A and 3B show the hydrophobicity plots (MacDNASIS PRO software) for HHFP (SEQ ID NO: 1) and rat mH2A (SEQ ID NO:3). The positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

HHFP, as used herein, refers to the amino acid sequences of substantially purified HHFP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GELVIEW™ Fragment Assembly system (GCG, Madison, Wis.), or which has been both extended and assembled.

A "variant" of HHFP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HHFP, or any oligopeptide thereof, to induce a specific immune response in appropriate animals or cells and to bind with specific antibodies.

The term "agonist", as used herein, refers to a molecule which, when bound to HHFP, causes a change in HHFP which modulates the activity of HHFP. Agonists may include proteins, nucleic acids, carbohydrates, or any other molecules which bind to HHFP.

The terms "antagonist" or "inhibitor", as used herein, refer to a molecule which, when bound to HHFP, blocks or modulates the biological or immunological activity of HHFP. Antagonists and inhibitors may include proteins, nucleic acids, carbohydrates, or any other molecules which bind to HHFP.

The term "modulate", as used herein, refers to a change or an alteration in the biological activity of HHFP. Modulation may be an increase or a decrease in protein activity, a change in binding characteristics, or any other change in the biological, functional or immunological properties of HHFP.

The term "mimetic", as used herein, refers to a molecule, the structure of which is developed from knowledge of the structure of HHFP or portions thereof and, as such, is able to effect some or all of the actions of the molecules related to the histone fusion protein.

The term "derivative", as used herein, refers to the chemical modification of a nucleic acid encoding HHFP or the encoded HHFP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human HHFP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HHFP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding HHFP in a sample and thereby correlates with expression of the transcript from the polynucleotide encoding the protein.

"Alterations" in the polynucleotide of SEQ ID NO: 2, as used herein, comprise any alteration in the sequence of polynucleotides encoding HHFP including deletions, insertions, and point mutations that may be detected using hybridization assays. Included within this definition is the detection of alterations to the genomic DNA sequence which encodes HHFP (e.g., by alterations in the pattern of restriction fragment length polymorphisms capable of hybridizing to SEQ ID NO:2), the inability of a selected fragment of SEQ ID NO: 2 to hybridize to a sample of genomic DNA (e.g., using allele-specific oligonucleotide probes), and improper or unexpected hybridization, such as hybridization to a locus other than the normal chromosomal locus for the polynucleotide sequence encoding HHFP (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind HHFP polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of a novel human histone fusion protein (HHFP), the polynucleotides encoding HHFP, and the use of these compositions for the diagnosis, prevention, or treatment of disorders associated with cell proliferation and inflammation.

Nucleic acids encoding the human HHFP of the present invention were first identified in Incyte Clone 2297753 from a breast tissue cDNA library (BRSTNOT05) through a computer-generated search for amino acid sequence alignments. A consensus sequence, SEQ ID NO:2, was derived from the following overlapping and/or extended nucleic acid sequences: Incyte Clones 1231365 (BRAITUT01), 2624843 (PROSTUT12), 1973967 (UCMCL5T01), 2194366 (THYRTUT03), 1378730 (LUNGNOT10), 2297753 (BRSTNOT05), 2621562 (KERANOT02), 703884 (SYNORAT04), 1986585 (LUNGAST01), 1749085 (STOMTUT02), 2506474 (CONUTUT01), and 371282 (LUNGNOT02).

Figure 2B:
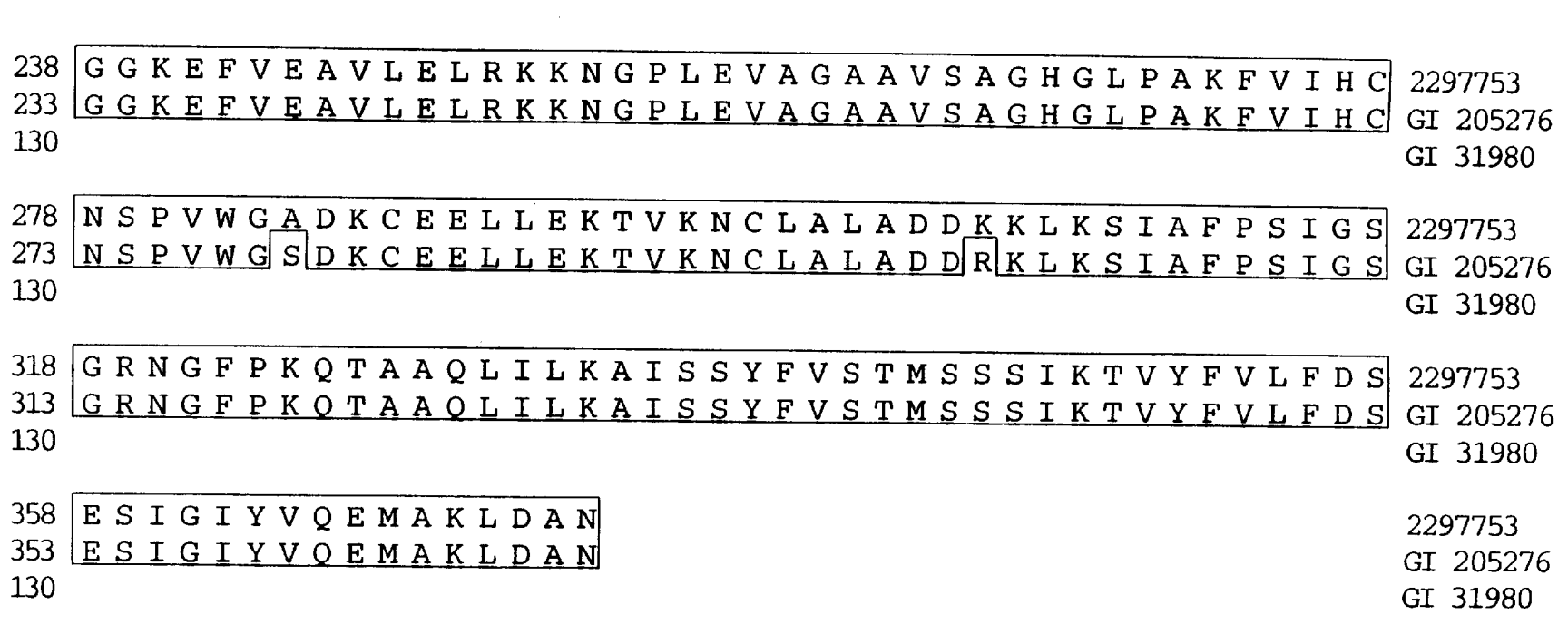
Figure 3B:
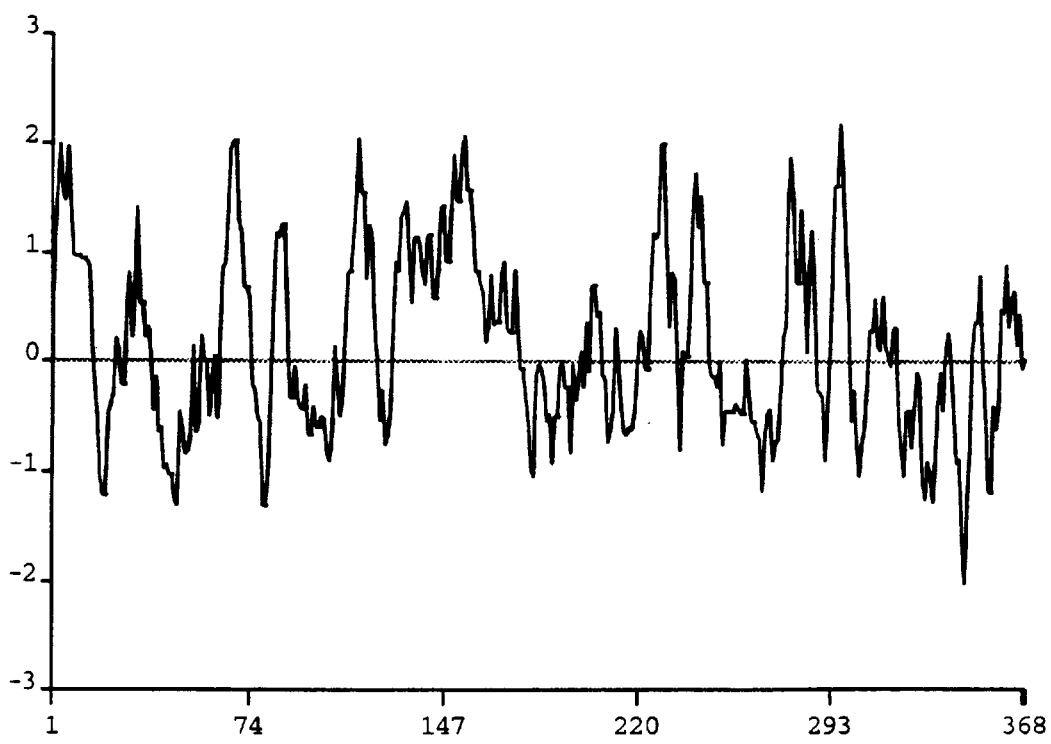

In one embodiment, the invention encompasses a polypeptide comprising the amino acid sequence of SEQ ID NO: 1, as shown in FIGS. 1A–E. HHFP is 373 amino acids in length and has three potential cAMP- or cGMP-dependent protein kinase phosphorylation sites at tS K7-S10, K8-T11, and K117-S120, a casein kinase II phosphorylation site at T220-D223, and 12 protein kinase C phosphorylation sites at S2-R4, S10-K12, T13-R15, S16-K18, T77-R79, S140-K142, S146-K148, S158-K160, S188-K190, T294-K296, S317-R319, and S346-K348. As shown in FIGS. 2A and 2B, the amino terminus of HHFP resembles the full length human H2A. Residues 133–161 of HHFP are highly basic and have similarity with the carboxy terminus of histone H1, indicating the DNA-binding potential of HHFP. A leucine zipper region is identified between residues 183 and 213 of HHFP. This is similar to rat mH2A, indicating a potential transcription-regulating function of HHFP. HHFP has chemical and structural homology with rat mH2A (GI 205276; SEQ ID NO:3) and human H2A (GI 31980; SEQ ID NO 4). In particular, HHFP and rat mH2A share 90% identity. As illustrated by FIGS. 3A and 3B, HHFP and rat mH2A have rather similar hydrophobicity plots. Northern analysis shows the expression of this sequence in various cDNA libraries, at least 49% of which are immortalized or cancerous and at least 27% of which involve immune response.

The invention also encompasses HHFP variants. A preferred HHFP variant is one having at least 80%, and more preferably 90%, amino acid sequence identity to the HHFP amino acid sequence (SEQ ID NO:1). A most preferred HHFP variant is one having at least 95% amino acid sequence identity to SEQ ID NO:1.

The invention also encompasses polynucleotides which encode HHFP. Accordingly, any nucleic acid sequence which encodes the amino acid sequence of HHFP can be used to generate recombinant molecules which express HHFP. In a particular embodiment, the invention encompasses the polynucleotide comprising the nucleic acid sequence of SEQ ID NO:2 as shown in FIG. 1.

It will be appreciated by those skilled in the art that as a result of the degeneracy of the genetic code, a multitude of nucleotide sequences encoding HHFP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HHFP, and all such variations are to be considered as being specifically disclosed.

Although nucleotide sequences which encode HHFP and its variants are preferably capable of hybridizing to the nucleotide sequence of the naturally occurring HHFP under appropriately selected conditions of stringency, it may be advantageous to produce nucleotide sequences encoding HHFP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HHFP and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode HHFP and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding HHFP or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding HHFP which are encompassed by the invention include deletions, insertions, or substitutions of different nucleotides resulting in a polynucleotide that encodes the same or a functionally equivalent HHFP. The encoded protein may also contain deletions, insertions, or substitutions of amino acid residues which produce a silent change and result in a functionally equivalent HHFP. Deliberate amino acid substitutions may be made on the basis of similarity in polarity, charge, solubility, hydrophobicity, hydrophilicity, and/or the amphipathic nature of the residues as long as the biological activity of HHFP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding HHFP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding HHFP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions. to Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HHFP, or fusion proteins or functional equivalents thereof, may be used in recombinant DNA molecules to direct expression of HHFP in appropriate host cells. Due to the inherent degeneracy of the genetic code, other DNA sequences which encode substantially the same or a functionally equivalent amino acid sequence may be produced and these sequences may be used to clone and express HHFP.

As will be understood by those of skill in the art, it may be advantageous to produce HHFP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter HHFP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding HHFP may be ligated to a heterologous sequence to encode a fusion protein. For example, to screen peptide libraries for inhibitors of HHFP activity, it may be useful to encode a chimeric HHFP protein that can be recognized by a commercially available antibody. A fusion protein may also be engineered to contain a cleavage site located between the HHFP encoding sequence and the heterologous protein sequence, so that HHFP may be cleaved and purified away from the heterologous moiety.

In another embodiment, sequences encoding HHFP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HHFP, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HHFP, or any part thereof, may be altered during direct synthesis and/or combined using chemical methods with sequences from other proteins, or any part thereof, to produce a variant polypeptide.

In order to express a biologically active HHFP, the nucleotide sequences encoding HHFP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HHFP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding HHFP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HHFP, vectors based on SV40 or EBV may be used with an appropriate selectable marker.

In bacterial systems, a number of expression vectors may be selected depending upon the use intended for HHFP. For example, when large quantities of HHFP are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding HHFP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HHFP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991)

Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HHFP. For example, in one such system, *Autographa califomica* nuclear polyhedrosis virus (AcNPV) is used as a vector to express foreign genes in *Spodoptera frugiperda* cells or in *Trichoplusia larvae*. The sequences encoding HHFP may be cloned into a non-essential region of the virus, such as the polyhedrin gene, and placed under control of the polyhedrin promoter. Successful insertion of HHFP will render the polyhedrin gene inactive and produce recombinant virus lacking coat protein. The recombinant viruses may then be used to infect, for example, *S. frugiperda* cells or *Trichoplusia larvae* in which HHFP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HHFP may be ligated into an adenovirus transcription/translation complex consisting of the late promoter and tripartite leader sequence. Insertion in a non-essential E1 or E3 region of the viral genome may be used to obtain a viable virus which is capable of expressing HHFP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding HHFP. Such signals include the ATG initiation codon and adjacent sequences. In cases where sequences encoding HHFP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HHFP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HHFP is inserted within a marker gene sequence, recombinant cells containing sequences encoding HHFP can be identified by the absence of marker gene function. Alternatively, a marker gene can be placed in tandem with a sequence encoding HHFP under the control of a single promoter. Expression of the marker gene in response to induction or selection usually indicates expression of the tandem gene as well.

Alternatively, host cells which contain the nucleic acid sequence encoding HHFP and express HHFP may be identified by a variety of procedures known to those of skill in the art. These procedures include, but are not limited to, DNA—DNA or DNA-RNA hybridizations and protein bioassay or immunoassay techniques which include membrane, solution, or chip based technologies for the detection and/or quantification of nucleic acid or protein.

The presence of polynucleotide sequences encoding HHFP can be detected by DNA—DNA or DNA-RNA hybridization or amplification using probes or portions or fragments of polynucleotides encoding HHFP. Nucleic acid amplification based assays involve the use of oligonucleotides or oligomers based on the sequences encoding HHFP to detect transformants containing DNA or RNA encoding HHFP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HHFP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HHFP is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HHFP include oligolabeling, nick translation, end-labeling or PCR amplification using a labeled nucleotide. Alternatively, the sequences encoding HHFP, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalarnazoo, Minn.); Promega (Madison Wis.); and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding HHFP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HHFP may be designed to contain signal sequences which direct secretion of HHFP through a prokaryotic or eukaryotic cell membrane. Other recombinant constructions may be used to join sequences encoding HHFP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HHFP may be used to facilitate purification. One such expression vector provides for expression of a fusion protein containing HHFP and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3: 263–281) while the enterokinase cleavage site provides a means for purifying HHFP from the fusion protein. A discussion of vectors which contain fusion proteins is provided in Kroll, D. J. et al. (1993; DNA Cell Biol. 12:441–453).

In addition to recombinant production, fragments of HHFP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of HHFP may be chemically synthesized separately and combined using chemical methods to produce the full length molecule.

Therapeutics

HHFP shares chemical and structural homology with the rat mH2A (GI 205276) and the human histone H2A (GI 31980). Northern analysis shows that the expression of HHFP is associated with cell proliferation and inflammation.

Therefore, in one embodiment, HHFP or a fragment or derivative thereof may be added to cells to stimulate cell proliferation. In particular, HHFP may be added to a cell or cells in vivo using delivery mechanisms such as liposomes, viral based vectors, or electroinjection for the purpose of promoting regeneration or differentiation of the cell or cells. In addition, HHFP may be added to a cell, cell line, tissue or organ culture in vitro or ex vivo to stimulate cell proliferation for use in heterologous or autologous transplantation. In some cases, the cell will have been selected for its ability to fight an infection or a cancer or to correct a genetic defect such as sickle cell anemia, β thalassemia, etc. In another embodiment, an agonist which is specific for HHFP may be used to stimulate cell proliferation, as detailed above. In still another embodiment, a vector capable of expressing HHFP, or a fragment or a derivative thereof, may be used to stimulate cell proliferation, as detailed above.

In another embodiment, an antagonist or an inhibitor of HHFP, or a fragment or a derivative thereof, may be administered to a subject to prevent or treat a disorder associated with cell proliferation. Disorders of cell proliferation include various types of cancer including, but not limited to, adenocarcinoma, sarcoma, lymphoma, leukemia, and cancers of the bladder, bone, brain, breast, colon, heart, kidney, liver, lung, ovary, pancreas, paraganglia, parathyroid, prostate, skin, intestine, testis, thyroid, tongue, and uterus. In still aother embodiment, a vector expressing the complementary sequence or antisense of the polynucleotide encoding HHFP, or a fragment or a derivative thereof, may be administered to a subject to prevent or treat a disorder associated with cell proliferation including, but not limited to, those listed above. In one aspect, an antibody specific for HHFP may be used directly as an antagonist, or indirectly as a targeting or delivery mechanism for bringing a pharmaceutical agent to cells or tissue which express HHFP.

In a further embodiment, an antagonist or an inhibitor of HHFP or a fragment or a derivative thereof, may be administered to a subject to prevent or treat a disorder associated with inflammation. Disorders of inflammation include, but are not limited to, AIDS, Addison's disease, allergies, asthma, bronchitis, Crohn's disease, dermatomyositis, diabetes mellitus, emphysema, Graves' disease, irritable bowel syndrome, lupus erythematosus, myasthenia gravis, multiple sclerosis, urethritis, rheumatoid and osteoarthritis, thyroiditis, and ulcerative colitis. In still further embodiment, a vector expressing the complementary sequence or antisense of the polynucleotide encoding HHFP, or a fragment or a derivative thereof, may be administered to a subject to prevent or treat a disorder associated with inflammation including, but not limited to, those listed above. In one aspect, an antibody specific for HHFP may be used directly as an antagonist, or indirectly as a targeting or delivery mechanism for bringing a pharmaceutical agent to cells or tissue which express HHFP.

In other embodiments, any of the therapeutic proteins, antagonists, antibodies, agonists, complementary or antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of HHFP may be produced using methods which are generally known in the art. In particular, purified HHFP may be used to produce antibodies or to screen libraries of pharmaceutical agents to identify those which specifically bind HHFP.

Antibodies to HHFP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HHFP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HHFP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HHFP amino acids may be fused with those of another protein such as keyhole limpet hemocyanin and antibody produced against the chimeric molecule.

Monoclonal antibodies to HHFP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HHFP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies specific for HHFP may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for HHFP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HHFP and its specific antibody. A two-site, monoclonal-based immunoassay utilizing monoclonal antibodies reactive to two non-interfering HHFP epitopes is preferred, but a competitive binding assay may also be employed (Maddox, supra).

In another embodiment of the invention, the polynucleotides encoding HHFP, or any fragment thereof, or antisense molecules, may be used for therapeutic purposes. In one aspect, antisense to the polynucleotide encoding HHFP may be used in situations in which it would be desirable to block the transcription of the mRNA. In particular, cells may be transformed with sequences complementary to polynucleotides encoding HHFP. Thus, antisense molecules may be used to modulate HHFP activity, or to achieve regulation of gene function. Such technology is now well known in the art, and sense or antisense oligomers or larger fragments, can be designed from various locations along the coding or control regions of sequences encoding HHFP.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding HHFP. These techniques are described both in Sambrook et al. (supra) and in Ausubel et al. (supra).

Genes encoding HHFP can be turned off by transforming a cell or tissue with expression vectors which express high levels of a polynucleotide or fragment thereof which encodes HHFP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HHFP, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HHFP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HHFP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HHFP, antibodies to HHFP, mimetics, agonists, antagonists, or inhibitors of HHFP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HHFP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HHFP or fragments thereof, antibodies of HHFP, agonists, antagonists or inhibitors of HHFP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HHFP may be used for the diagnosis of conditions or diseases characterized by expression of HHFP, or in assays to monitor patients being treated with HHFP, agonists, antagonists or inhibitors. The antibodies useful for diagnostic purposes may be prepared in the same manner as those described above for therapeutics. Diagnostic assays for HHFP include methods which utilize the antibody and a label to detect HHFP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HHFP are known in the art and provide a basis for diagnosing altered or abnormal levels of HHFP expression. Normal or standard values for HHFP expression are established by combining body fluids or cell extracts taken from normal mammalian subjects, preferably human, with antibody to HHFP under conditions suitable for complex formation. The amount of standard complex formation may be quantified by various methods, but preferably by photometric means. Quantities of HHFP expressed in subject, control, and disease samples from biopsied tissues are compared with the standard values. Deviation between standard and subject values establishes the parameters for diagnosing disease.

In another embodiment of the invention, the polynucleotides encoding HHFP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HHFP may be correlated with disease. The diagnostic assay may be used to distinguish between absence, presence, and excess expression of HHFP, and to monitor regulation of HHFP levels during therapeutic intervention.

In one aspect, hybridization with PCR probes which are capable of detecting polynucleotide sequences, including genomic sequences, encoding HHFP or closely related molecules, may be used to identify nucleic acid sequences which encode HHFP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HHFP, alleles, or related sequences.

Probes may also be used for the detection of related sequences, and should preferably contain at least 50% of the nucleotides from any of the HHFP encoding sequences. The hybridization probes of the subject invention may be DNA or RNA and derived from the nucleotide sequence of SEQ ID NO:2 or from genomic sequence including promoter, enhancer elements, and introns of the naturally occurring HHFP.

Means for producing specific hybridization probes for DNAs encoding HHFP include the cloning of nucleic acid sequences encoding HHFP or HHFP derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HHFP may be used for the diagnosis of disorders associated with the expression of HHFP. Examples of such disorders include: various types of cancer such as adenocarcinoma, sarcoma, lymphoma, leukemia, and cancers of the bladder, bone, brain, breast, colon, heart, kidney, liver, lung, ovary, pancreas, paraganglia, parathyroid, prostate, skin, intestine, testis, thyroid, tongue, and uterus; disorders associated with inflammation such as AIDS, Addison's disease, allergies, asthma, bronchitis, Crohn's disease, dermatomyositis, diabetes mellitus, emphysema, Graves' disease, irritable bowel syndrome, lupus erythematosus, myasthenia gravis, multiple sclerosis, urethritis, rheumatoid and osteoarthritis, thyroiditis, and ulcerative colitis. The polynucleotide sequences encoding HHFP may be used in Southern or northern analysis, dot blot, or other membrane-based technologies; in PCR technologies; or in dip stick, pin, ELISA or chip assays utilizing fluids or tissues from patient biopsies to detect altered HHFP expression. Such qualitative or quantitative methods are well known in the art.

In a particular aspect, the nucleotide sequences encoding HHFP may be useful in assays that detect activation or induction of various cancers, particularly those mentioned above. The nucleotide sequences encoding HHFP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HHFP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HHFP, a normal or standard profile for expression is established. This may be accomplished by combining body fluids or cell extracts taken from normal subjects, either animal or human, with a sequence, or a fragment thereof, which encodes HHFP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HHFP may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HHFP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequences which encode HHFP may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding HHFP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HHFP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HHFP and the agent being tested, may be measured.

Another technique for drug screening which may be used provides for high throughput screening of compounds having suitable binding affinity to the protein of interest as described in published PCT application WO84/03564. In this method, as applied to HHFP large numbers of different small test compounds are synthesized on a solid substrate, such as plastic pins or some other surface. The test compounds are reacted with HHFP, or fragments thereof, and washed. Bound HHFP is then detected by methods well known in the art. Purified HHFP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HHFP specifically compete with a test compound for binding HHFP. In this manner, the antibodies can be used to detect the presence of any peptide which shares one or more antigenic determinants with HHFP.

In additional embodiments, the nucleotide sequences which encode HHFP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BRSTNOT05 cDNA Library Construction

The BRSTNOT05 cDNA library was constructed from microscopically normal breast tissue obtained from a 58-year-old Caucasian female who had undergone an unilateral extended simple mastectomy following diagnosis of multicentric invasive grade 4 mammary lobular carcinoma. Pathology of the non-tumorous breast tissue was negative for tumor. Tumor cells forming a single predominant mass were identified in the upper outer quadrant of the left breast and three separate nodules were found in the lower outer quadrant of the left breast. The surgical margins were found negative for tumor. The skin, nipple, and fascia were uninvolved. No evidence of vascular invasion was found. Eight mid low and two high left axillary lymph nodes were negative for tumor. Prior to surgery, the patient was prescribed tamoxifen to inhibit the induction of mammary carcinoma.

The frozen tissue was homogenized and lysed using a Brinkmann Homogenizer Polytron PT-3000 (Brinkmann Instruments, Westbury, N.Y.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. Extraction and precipitation were repeated as before. The mRNA was isolated with the Qiagen Oligotex kit (QIAGEN, Inc.; Chatsworth, Calif.) and used to construct the cDNA library.

The mRNA was handled according to the recommended protocols in the SuperScript Plasmid System for cDNA Synthesis and Plasmid Cloning (Catalog #18248-013, Gibco/RRL, Gaithersburg, Md.). cDNAs were fractionated on a Sepharose CL4B column (Catalog #275105-01, Pharmacia), and those cDNAs exceeding 400 bp were ligated into pSport 1. The plasmid pSport 1 was subsequently transformed into DH5a™ competent cells (Catalog #18258-012, Gibco/BRL).

II Isolation and Sequencing of cDNA Clones

Plasmid DNA was released from the cells and purified using the REAL Prep 96 Plasmid Kit (Catalog #26173; QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III Homology Searching of cDNA Clones and Their Deduced Proteins

After the reading frame was determined, the nucleotide sequences of the Sequence Listing or amino acid sequences deduced from them were used as query sequences against databases such as GenBank, SwissProt, BLOCKS, and Pima II. These databases which contain previously identified and annotated sequences, were searched for regions of homology (similarity) using BLAST, which stands for Basic Local Alignment Search Tool (Altschul (1993) supra, Altschul (1990) supra).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach, as detailed in Karlin et al. (supra) and incorporated herein by reference, searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-14}$ for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HHFP occurs. Abundance and percent abundance are also reported. Abundance directly reflects the number of times a particular transcript is represented in a cDNA library, and percent abundance is abundance divided by the total number of sequences examined in the cDNA library.

V Extension of HHFP-Encoding Polynucleotides

Nucleic acid sequence of Incyte clone 1597102 or SEQ ID NO:2 is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M.J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQuick™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 µl of liquid LB/2x Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3x) containing 4 units of rTth DNA polymerase, a vector primer, and one or both of the gene specific primers used for the extension reaction are added to each well. Amplification is performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers, The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of [γ-$^{32}$P] adenosine triphosphate (Amersham) and T4 polynucleotide kinase (DuPont NEN™, Boston, Mass.). The labeled oligonucleotides are substantially purified with Sephadex G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba I, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

Antisense molecules or nucleic acid sequences complementary to the HHFP-encoding sequence, or any part thereof, are used to inhibit in vivo or in vitro expression of naturally occurring HHFP. Although use of antisense oligonucleotides, comprising about 20 base-pairs, is specifically described, essentially the same procedure is used with larger cDNA fragments. An oligonucleotide based on the coding sequences of HHFP, as shown in FIG. 1, is used to inhibit expression of naturally occurring HHFP. The complementary oligonucleotide is designed from the most unique 5' sequence as shown in FIG. 1 and used either to inhibit transcription by preventing promoter binding to the upstream nontranslated sequence or translation of an HHFP-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIG. 1.

VIII Expression of HHFP

Expression of HHFP is accomplished by subcloning the cDNAs into appropriate vectors and transforming the vectors into host cells. In this case, the cloning vector, pSport, previously used for the generation of the cDNA library is used to express HHFP in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HHFP into the bacterial growth media which can be used directly in the following assay for activity.

IX Demonstration of HHFP Activity

Cell lines or tissues transformed with a vector containing SEQ ID NO:1 can be assayed for HHFP activity by immunoblotting. Cells are denatured by SDS in the presence of β-mercaptoethanol, nucleic acids removed by ethanol precipitation, and proteins purified by acetone precipitation. Pellets are resuspended in 20 mM tris buffer at pH 7.5 and incubated with Protein G-Sepharose pre-coated with an antibody specific for HHFP. After washing, the Sepharose beads are boiled in electrophoresis sample buffer, and the eluted proteins subjected to SDS-PAGE. The SDS-PAGE is transferred to a nitrocellulose membrane for immunoblotting, and the HHFP activity is assessed by visualizing and quantifying bands on the blot using the antibody specific for HHFP as the primary antibody and $^{125}$I-labeled IgG specific for the primary antibody as the secondary antibody.

X Production of HHFP Specific Antibodies

HHFP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring HHFP Using Specific Antibodies

Naturally occurring or recombinant HHFP is substantially purified by immunoaffinity chromatography using antibodies specific for HHFP. An immunoaffinity column is constructed by covalently coupling HHFP antibody to an activated chromatographic resin, such as CnBr-activated Sepharose (Pharmacia & Upjohn). After the coupling, the resin is blocked and washed according to the manufacturer's instructions.

Media containing HHFP is passed over the immunoaffinity column, and the column is washed under conditions that allow the preferential absorbance of HHFP (e.g., high ionic strength buffers in the presence of detergent). The column is eluted under conditions that disrupt antibody/HHFP binding (eg, a buffer of pH 2–3 or a high concentration of a chaotrope, such as urea or thiocyanate ion), and HHFP is collected.

XII Identification of Molecules Which Interact with HHFP

HHFP or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HHFP, washed and any wells with labeled HHFP complex are assayed. Data obtained using different concentrations of HHFP are used to calculate values for the number, affinity, and association of HHFP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. A substantially purified human histone fusion protein comprising the amino acid sequence of SEQ ID NO: 1.

2. A pharmaceutical composition comprising a substantially purified human histone fusion protein having the amino acid sequence of SEQ ID NO: 1 in conjunction with a suitable pharmaceutical carrier.

3. A method for stimulating cell proliferation comprising adding to a cell an effective amount of the protein of claim 1.

4. A method for using a protein to screen a library of other molecules for a molecule which specifically binds the protein, the method comprising:

(a) combining the protein of claim 1 with the library of molecules under conditions suitable to allow complex formation, and (b) detecting complex formation, wherein the presence of the complex identifies a molecule which specifically binds the protein.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 373 amino acids
      (B) TYPE: amino acid
      (C) STRANDEDNESS: single
      (D) TOPOLOGY: linear (vii) IMMEDIATE SOURCE:
      (A) LIBRARY: BRSTNOT05
      (B) CLONE: 2297753

(xi) SEQUENCE DESCRIPTION: SEQ ID NO:1:

```
Met Ser Ser Arg Gly Gly Lys Lys Ser Thr Lys Thr Ser Arg Ser
1               5                   10                  15

Ala Lys Ala Gly Val Ile Phe Pro Val Gly Arg Met Leu Arg Tyr Ile
            20                  25                  30

Lys Lys Gly His Pro Lys Tyr Arg Ile Gly Val Gly Ala Pro Val Tyr
            35                  40                  45

Met Ala Ala Val Leu Glu Tyr Leu Thr Ala Glu Ile Leu Glu Leu Ala
    50                  55                  60

Gly Asn Ala Ala Arg Asp Asn Lys Lys Gly Arg Val Thr Pro Arg His
65                  70                  75                  80

Ile Leu Leu Ala Val Ala Asn Asp Glu Glu Leu Asn Gln Leu Leu Lys
                85                  90                  95

Gly Val Thr Ile Ala Ser Gly Gly Val Leu Pro Asn Ile His Pro Glu
                100                 105                 110

Leu Leu Ala Lys Lys Arg Gly Ser Lys Gly Lys Leu Glu Ala Ile Ile
            115                 120                 125

Thr Pro Pro Pro Ala Lys Lys Ala Lys Ser Pro Ser Gln Lys Lys Pro
    130                 135                 140

Val Ser Lys Lys Ala Gly Gly Lys Lys Gly Ala Arg Lys Ser Lys Lys
145                 150                 155                 160
```

```
Lys Gln Gly Glu Val Ser Lys Ala Ala Ser Ala Asp Ser Asn Asn Arg
            165                 170                 175

Gly Glu His Leu Pro Asp Gly Phe Thr Val Leu Ser Thr Lys Ser Leu
            180                 185                 190

Phe Leu Gly Gln Lys Leu Asn Leu Ile His Ser Glu Ile Ser Asn Leu
            195                 200                 205

Ala Gly Phe Glu Val Glu Ala Ile Ile Asn Pro Thr Asn Ala Asp Ile
            210                 215                 220

Asp Leu Lys Asp Asp Leu Gly Asn Thr Leu Glu Lys Lys Gly Gly Lys
225                 230                 235                 240

Glu Phe Val Glu Ala Val Leu Glu Leu Arg Lys Lys Asn Gly Pro Leu
            245                 250                 255

Glu Val Ala Gly Ala Ala Val Ser Ala Gly His Gly Leu Pro Ala Lys
            260                 265                 270

Phe Val Ile His Cys Asn Ser Pro Val Trp Gly Ala Asp Lys Cys Glu
            275                 280                 285

Glu Leu Leu Glu Lys Thr Val Lys Asn Cys Leu Ala Leu Ala Asp Asp
            290                 295                 300

Lys Lys Leu Lys Ser Ile Ala Phe Pro Ser Ile Gly Ser Gly Arg Asn
305                 310                 315                 320

Gly Phe Pro Lys Gln Thr Ala Ala Gln Leu Ile Leu Lys Ala Ile Ser
            325                 330                 335

Ser Tyr Phe Val Ser Thr Met Ser Ser Ile Lys Thr Val Tyr Phe
            340                 345                 350

Val Leu Phe Asp Ser Glu Ser Ile Gly Ile Tyr Val Gln Glu Met Ala
            355                 360                 365

Lys Leu Asp Ala Asn
    370

(2) INFORMATION FOR SEQ ID NO:2:

(i) SEQUENCE CHARACTERISTICS:
        (A) LENGTH: 1827 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT05
        (B) CLONE: 2297753

(xi) SEQUENCE DESCRIPTION: SEQ ID NO:2:

CCAGGAGGGC TCAGGCCGAG ACACCTTGCA GCTGCCGCCG CCGCCACCGA GCCGCCGCTG      60

TGCTCACTGA TCCGCCTCCA GGGCCACCGC CATGTCGAGC CGCGGTGGGA AGAAGAAGTC     120

CACCAAGACG TCCAGGTCTG CCAAAGCAGG AGTCATCTTT CCCGTGGGGC GGATGCTGCG     180

GTACATCAAG AAAGGCCACC CCAAGTACAG GATTGGAGTG GGGGCACCCG TGTACATGGC     240

CGCCGTCCTG GAATACCTGA CAGCGGAGAT TCTGGAGCTG GCTGGCAATG CAGCGAGAGA     300

CAACAAGAAG GGACGGGTCA CACCCCGGCA CATCCTGCTG GCTGTGGCCA ATGATGAAGA     360

GCTGAATCAG CTGCTAAAAG GAGTCACCAT AGCCAGTGGG GGTGTGTTAC CAACATCCA     420

CCCCGAGTTG CTAGCGAAGA AGCGGGGATC CAAAGGAAAG TTGGAAGCCA TCATCACACC     480

ACCCCCAGCC AAAAAGGCCA AGTCTCCATC CCAGAAGAAG CCTGTATCTA AAAAAGCAGG     540

AGGCAAGAAA GGGGCCCGGA AATCCAAGAA GAAGCAGGGT GAAGTCAGTA AGGCAGCCAG     600

CGCCGACAGC AACAACCGAG GGAACACCT GCCCGACGGT TTCACAGTCC TCTCCACCAA     660
```

-continued

```
GAGCCTCTTC CTTGGCCAGA AGCTGAACCT TATTCACAGT GAAATCAGTA ATTTAGCCGG      720

CTTTGAGGTG GAGGCCATAA TCAATCCTAC CAATGCTGAC ATTGACCTTA AGATGACCT       780

AGGAAACACG CTGGAGAAGA AAGGTGGCAA GGAGTTTGTG GAAGCTGTCC TGGAACTCCG      840

GAAAAAGAAC GGGCCCTTGG AAGTAGCTGG AGCTGCTGTC AGCGCAGGCC ATGGCCTGCC      900

TGCCAAGTTT GTGATCCACT GTAATAGTCC AGTTTGGGGT GCAGACAAGT GTGAAGAACT      960

TCTGGAAAAG ACAGTGAAAA ACTGCTTGGC CCTGGCTGAT GATAAGAAGC TGAAATCCAT     1020

TGCATTTCCA TCCATCGGCA GCGGCAGGAA CGGTTTTCCA AAGCAGACAG CAGCTCAGCT     1080

GATTCTGAAG GCCATCTCCA GTTACTTCGT GTCTACAATG TCCTCTTCCA TCAAAACGGT     1140

GTACTTCGTG CTTTTTGACA GCGAGAGTAT AGGCATCTAT GTGCAGGAAA TGGCCAAGCT     1200

GGACGCCAAC TAGGCTGAGC AATGACAGAA CCAGCTGCAC CATGTACCCC ACCTTCAGTT     1260

TAAAAGAAAA AAAAAATCCC CTTCACTCCT ACTGGGAGGT GGGACCCCTT TCATTTTCAG     1320

TTTTGCTCAT CTAGGGAAAA TAAGGCTTTG GTTTCCAGTT TAATTGTTTT TGACCTTCTA     1380

AAATGTTTTT ATGTTAGCAC TGATAGTTGG CATTACTGTT GTTAAGCACT GTGTTCCAGA     1440

CCGTGTCTGA CTTAGTGTAA CCTAGGAGAT TTTATAGTTT TATTTTAATG AAACCCTGAT     1500

TGACGCACAG CAGTGGGGAG AACAGCGTCT TTTACCTGTC ACCGAAGCCC AGGAAGCCCC     1560

GTTTGTAAGC GTGTGTTGTG GTGCTTTATT GTACATCCTC CAGTGGCGTT CTTTTTACTC     1620

TAATGTTCTT TTGGTTTCCC CCCTCAGAAG AATCATGAAT TTGCAACAGA CCTAATTTTT     1680

GGTTACTTTT TGTCTTATTG ATGGATTTGA AAATGAAAGA TTTAATAAGG CAAAGCAGAA     1740

TCTGTTGTCC TTAATTATAT TTGCAATTTG GAATTTGTGT GAGTTGATTT AGTAAAATGT     1800

TAAACCGTTA AAAAAGAAA AAAAAAA                                         1827
```

(2) INFORMATION FOR SEQ ID NO:3:

(i) SEQUENCE CHARACTERISTICS:
        (A) LENGTH: 368 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 205276

(xi) SEQUENCE DESCRIPTION: SEQ ID NO:3:

```
Met Ser Ser Arg Gly Gly Lys Lys Ser Thr Lys Thr Ser Arg Ser
  1               5                  10                  15

Ala Lys Ala Gly Val Ile Phe Pro Val Gly Arg Met Leu Arg Tyr Ile
             20                  25                  30

Lys Lys Gly His Pro Lys Tyr Arg Ile Gly Val Gly Ala Pro Val Tyr
         35                  40                  45

Met Ala Ala Val Leu Glu Tyr Leu Thr Ala Glu Ile Leu Glu Leu Ala
     50                  55                  60

Gly Asn Ala Ala Arg Asp Asn Lys Lys Gly Arg Val Thr Pro Arg His
 65                  70                  75                  80

Ile Leu Leu Ala Val Ala Asn Asp Glu Glu Leu Asn Gln Leu Leu Lys
                 85                  90                  95

Gly Val Thr Ile Ala Ser Gly Gly Val Leu Pro Asn Ile His Pro Glu
            100                 105                 110

Leu Leu Ala Lys Lys Arg Gly Ser Lys Gly Lys Leu Glu Ala Ile Ile
            115                 120                 125
```

-continued

```
Thr Pro Pro Pro Ala Lys Lys Ala Lys Ser Pro Ser Gln Lys Lys Pro
    130                 135                 140

Val Ala Lys Lys Thr Gly Gly Lys Lys Gly Ala Arg Lys Ser Lys Lys
145                 150                 155                 160

Gln Gly Glu Val Ser Lys Ala Ala Ser Ala Asp Ser Thr Thr Glu Gly
                165                 170                 175

Ala Pro Thr Asp Gly Phe Thr Val Leu Ser Thr Lys Ser Leu Phe Leu
            180                 185                 190

Gly Gln Lys Leu Gln Val Val Gln Ala Asp Ile Ala Ser Ile Asp Ser
        195                 200                 205

Asp Ala Val Val His Pro Thr Asn Thr Asp Phe Tyr Ile Gly Gly Glu
    210                 215                 220

Val Gly Ser Thr Leu Glu Lys Lys Gly Gly Lys Glu Phe Val Glu Ala
225                 230                 235                 240

Val Leu Glu Leu Arg Lys Lys Asn Gly Pro Leu Glu Val Ala Gly Ala
                245                 250                 255

Ala Val Ser Ala Gly His Gly Leu Pro Ala Lys Phe Val Ile His Cys
            260                 265                 270

Asn Ser Pro Val Trp Gly Ser Asp Lys Cys Glu Glu Leu Leu Glu Lys
        275                 280                 285

Thr Val Lys Asn Cys Leu Ala Leu Ala Asp Asp Arg Lys Leu Lys Ser
    290                 295                 300

Ile Ala Phe Pro Ser Ile Gly Ser Gly Arg Asn Gly Phe Pro Lys Gln
305                 310                 315                 320

Thr Ala Ala Gln Leu Ile Leu Lys Ala Ile Ser Ser Tyr Phe Val Ser
                325                 330                 335

Thr Met Ser Ser Ser Ile Lys Thr Val Tyr Phe Val Leu Phe Asp Ser
            340                 345                 350

Glu Ser Ile Gly Ile Tyr Val Gln Glu Met Ala Lys Leu Asp Ala Asn
        355                 360                 365
```

(2) INFORMATION FOR SEQ ID NO:4:

(i) SEQUENCE CHARACTERISTICS:
        (A) LENGTH: 130 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 31980

(xi) SEQUENCE DESCRIPTION: SEQ ID NO:4:

```
Met Ser Gly Arg Gly Lys Gln Gly Gly Lys Ala Arg Ala Lys Ala Lys
1               5                   10                  15

Thr Arg Ser Ser Arg Ala Gly Leu Gln Phe Pro Val Gly Arg Val His
                20                  25                  30

Arg Leu Leu Arg Lys Gly Asn Tyr Ala Glu Arg Val Gly Ala Gly Ala
            35                  40                  45

Pro Val Tyr Leu Ala Ala Val Leu Glu Tyr Leu Thr Ala Glu Ile Leu
        50                  55                  60

Glu Leu Ala Gly Asn Ala Ala Arg Asp Asn Lys Lys Thr Arg Ile Ile
65                  70                  75                  80

Pro Arg His Leu Gln Leu Ala Ile Arg Asn Asp Glu Glu Leu Asn Lys
                85                  90                  95

Leu Leu Gly Lys Val Thr Ile Ala Gln Gly Gly Val Leu Pro Asn Ile
```

```
                    100                 105                 110
Gln Ala Val Leu Leu Pro Lys Lys Thr Glu Ser His His Lys Ala Lys
        115                 120                 125
Gly Lys
    130
```